United States Patent
Dvashi et al.

(10) Patent No.: US 10,682,328 B2
(45) Date of Patent: Jun. 16, 2020

(54) COMPOSITIONS AND METHODS FOR TREATMENT OF RETINAL DEGENERATIVE DISEASES

(71) Applicant: MOR RESEARCH APPLICATIONS LTD., Tel Aviv (IL)

(72) Inventors: Zeev Dvashi, Tel Aviv (IL); Ayala Pollack, Tel Aviv (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 15/532,116

(22) PCT Filed: Dec. 3, 2015

(86) PCT No.: PCT/IL2015/051174
§ 371 (c)(1),
(2) Date: Jun. 1, 2017

(87) PCT Pub. No.: WO2016/088125
PCT Pub. Date: Jun. 9, 2016

(65) Prior Publication Data
US 2017/0266146 A1 Sep. 21, 2017

Related U.S. Application Data

(60) Provisional application No. 62/086,985, filed on Dec. 3, 2014.

(51) Int. Cl.
| | |
|---|---|
| *A61K 31/223* | (2006.01) |
| *A61K 31/40* | (2006.01) |
| *A61K 9/00* | (2006.01) |
| *A61K 45/06* | (2006.01) |
| *A61K 38/05* | (2006.01) |
| *A61P 25/28* | (2006.01) |
| *A61P 27/02* | (2006.01) |

(52) U.S. Cl.
CPC .......... *A61K 31/223* (2013.01); *A61K 9/0019* (2013.01); *A61K 9/0048* (2013.01); *A61K 9/0051* (2013.01); *A61K 31/40* (2013.01); *A61K 38/05* (2013.01); *A61K 45/06* (2013.01); *A61P 25/28* (2018.01); *A61P 27/02* (2018.01)

(58) Field of Classification Search
CPC ...... A61K 31/223; A61K 38/05; A61K 45/06; A61K 9/0019; A61K 9/0051; A61K 9/0048; A61P 27/02; A61P 25/28
See application file for complete search history.

(56) References Cited

FOREIGN PATENT DOCUMENTS

CN 103656643 A * 3/2014
WO WO2009114729 9/2009

OTHER PUBLICATIONS

Jacobson, Lee S., et. Al. "Cathepsin-mediated necrosis controls the adaptive immune response by Th2 (T helper type 2)-associated adjuvants" Journal of Biological Chemistry 288.11 (2013)7481-7491, Jan. 7, 2013.
Tseng, Wen Allen, et al. "NLRP3 Inflammasome Activation in Retinal Pigment Epithelial Cells by Lysosomal Destabilization: Implications for Age-Related Macular DegenerationNLRP3 Inflammasome Activity in RPE Cells." Investigative ophthalmology & visual science 54.1 (2013): 110-120. Jan. 7, 2013.
Dvashi Z. & Pollack A., "Protective effect of TGF-?1 in RPE cells upon oxidative stress as a model for oxidative damage during dry AMD", ARVO 2013 Annual Meeting Abstracts by Scientific Section/ Group-Retinal Cell Biology, Vis. Sci. 54: E-Abstract 1805. pp. 72. Dec. 31, 2013.
Dvashi Z. & Pollack A., "TGF-?1 mediates RPE cell apoptosis through caspase-3 activation." Israeli society for vision and eye research, the 33rd annual meeting. Mar. 14-15, 2013, programs & abstracts pp. 132 URL:http://isver.org.il/wp-content/uploads/2013/03/ISVER-2013-Program-Abstracts-Book.pdf, Mar. 14, 2013.
Bree, R.T., et al., Cellular longevity: role of apoptosis and replicative senescence. Biogerontology, 2002. 3(4): p. 195-206.
Elmore, S., Apoptosis: a review of programmed cell death. Toxicol Pathol, 2007. 35(4): p. 495-516.
Blagosklonny, M.V., Cell cycle arrest is not senescence. Aging (Albany NY), 2011. 3(2): p. 94-101.
Vicencio, J.M., et al., Senescence, apoptosis or autophagy? When a damaged cell must decide its path—a mini-review. Gerontology, 2008. 54(2): p. 92-9.
Kuilman, T., et al., The essence of senescence. Genes Dev, 2010. 24(22): p. 2463-79.
Campisi, J. and F. d'Adda di Fagagna, Cellular senescence: when bad things happen to good cells. Nat Rev Mol Cell Biol, 2007. 8(9): p. 729-40.

* cited by examiner

*Primary Examiner* — Sahar Javanmard
(74) *Attorney, Agent, or Firm* — JMB Davis Ben-David

(57) ABSTRACT

This disclosure relates to compositions for use in treatment of Alzheimer's Disease, and/or a ocular and retinal degenerative disease, such as age related macular degeneration. The described compositions include effective amounts of LLMe, the hydrobromide form thereof, or functional derivatives thereof. Methods of treatment of a retinal degenerative disease of Alzheimer's Disease using the described compositions are also provided.

7 Claims, 12 Drawing Sheets

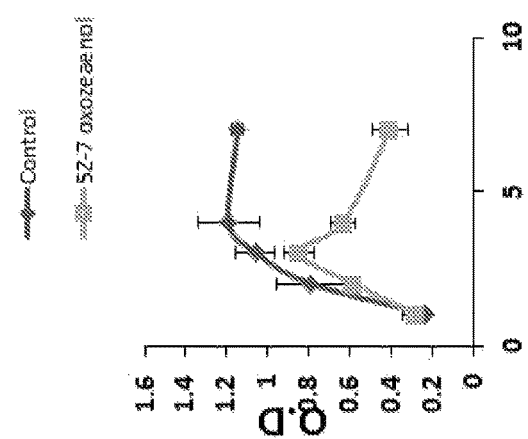
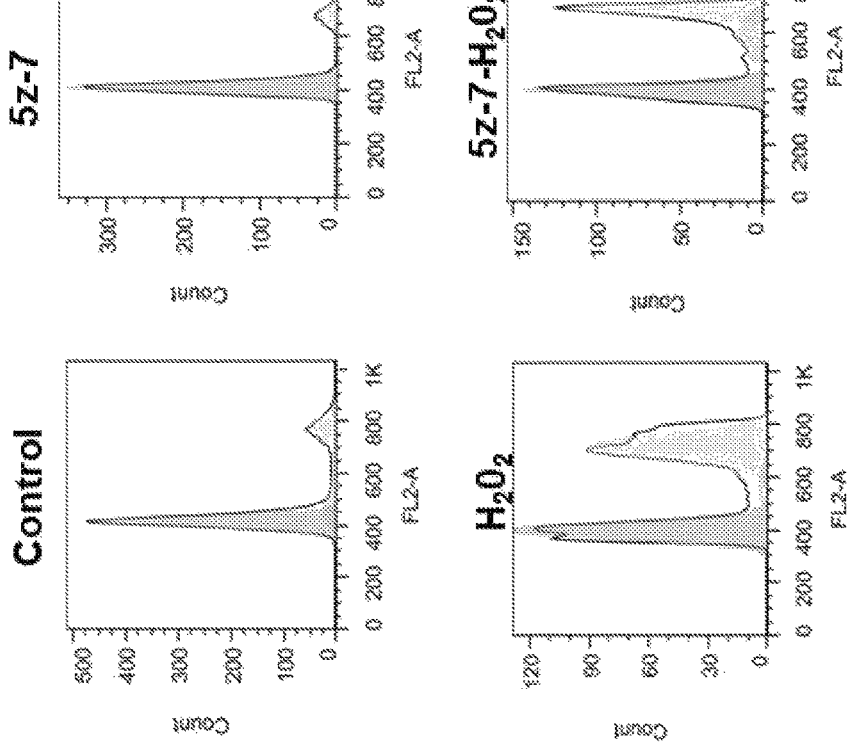

COMPOSITIONS AND METHODS FOR TREATMENT OF RETINAL DEGENERATIVE DISEASES

CROSS REFERENCE TO RELATED APPLICATIONS

This is the U.S. National Stage of International Application No. PCT/IL2015/051174, filed Dec. 3, 2015, which was published in English under PCT Article 21(2), and which in turn claims the benefit of U.S. Provisional Patent Application No. 62/086,985, filed on Dec. 3, 2014; the contents of which are incorporated by reference herein in their entirety.

FIELD

This disclosure relates to compositions for use in treatment of a senescence-related degenerative diseases, for example, retinal degenerative disease, such as age related macular degeneration, Retinitis Pigmentosa, diabetic retinopathy, and ocular pathologies such as: familial drusen, glaucoma, Stargardt's and Best disease. In addition neurodegenerative diseases, such as Alzheimer's disease. The described compositions include pharmaceutical agents including LLMe, and optionally, agents for activating p38 and/or JNK signaling in the retinal pigment epithelium or neuronal cells of a subject diagnosed with the disease. Methods of treatment of senescence-related degenerative diseases, including a retinal degenerative and/or neurodegenerative diseases using the described compositions are also provided.

BACKGROUND

Age-related macular degeneration (AMD) remains a major cause of blindness in the industrial world (1). The frequency of AMD increases with age, affecting 2% of the population at age 50, and 25% by age 80; and affects as many as 1.5 million Americans, and millions more around the world. There are two forms of AMD: "dry" and "wet". Dry AMD affects 85-90% of people with AMD, and is a chronic, asymptomatic disease that at the early stages may cause some degree of visual impairment, and may progress to legal blindness in the advanced stage of the disease. In the early stages of dry AMD, insoluble extracellular aggregates called drusen accumulate in the retina and are associated with decreased vision (1). The late stage of dry AMD, also known as geographic atrophy (GA), is characterized by scattered or confluent areas of degeneration of retinal pigment epithelial (RPE) cells and the overlying light-sensing retinal photoreceptor cells, which rely on the RPE for trophic support.

Wet AMD affects only 10%-15% of AMD patients, emerges abruptly and rapidly progresses to blindness. The advanced stage of the wet AMD is characterized by choroidal neovascularization (CNV), wherein new choroidal blood vessels emerge from the choroid toward the outer retina. Since the main pathology of wet AMD is the formation of new blood vessels, treatment of affected patients with anti-angiogenesis drugs have been proposed to reduce the risk of blindness. Accordingly, anti-angiogenic drugs such as bevacizumab and ranibizumab are commonly prescribed to treat for wet AMD, and which have been proven to halt the deterioration of vision and benefit many wet AMD patients.

Little is known about the growth factor and microenvironment mediating pathologic changes in early and advanced forms of dry AMD. In 2001, the Age-Related Eye Disease Study showed that daily high doses of the antioxidants beta-carotene, vitamins C and E, zinc, and copper decreased the risk of progression from early to advanced AMD in patients with intermediate forms of dry AMD (2). Other treatment strategies proposed for dry AMD include modulation of the visual cycle. By disrupting the conversion of retinol to rhodopsin, the key metabolite of phototransduction, toxic waste products such as lipofuscin and are decreased in the RPE (3). Proposed treatments to this end include ACU-4429 and fenretinide. Fenretinide is a synthetic retinoid derivative that competes with retinol in the circulation by binding retinol-binding protein. The ensuing complex is small enough to be excreted through the kidneys, thereby decreasing the available pool of retinol for uptake at the RPE. Additionally, International Patent Publication No. WO 2006/127945 discloses compounds and compositions that have been shown to reduce the formation of A2E. These compounds are designed to inhibit A2E biosynthesis by reducing the amount of free RAL available for reaction with PE in photoreceptor outer segments, which is the first step in the A2E biosynthetic pathway.

Other approaches for treating macular degeneration have been proposed, including use of neurotrophic receptor agonists, anti-inflammatory compounds including complement cascade inhibitors, anti-apoptosis compounds, steroids and anti-oxidant compounds (1). However, these and the other described treatments do not address the pathological cellular degeneration and senescence of the RPE cells that are most closely associated with the disease.

Similarities exist between AMD and Alzheimer's disease (AD). Both are neurodegenerative diseases, occurring at advancing age, both are associated with deposit formation such as amyloid (beta-amyloid) plaques in AD and drusen (beta-amyloid, apoE protein, complement components) in AMD. Additionally, both AMD and AD are associated with cellular senescence. The neurofibrillary tangles and neuritic components of the plaques of patients with AD show strong immunoreactivity for p16Ink4 (marker for senescence), but not for other members of this cell-cycle regulatory family. This biomarker of aging is not expressed in terminally differentiated neurons, demonstrating that the diseased neurons have acquired the expression of at least one senescence-associated protein. In AMD, markers of senescence, such as telomere shortening and altered gene expression have been identified in RPE cells exposed to advanced glycation end products (AGE), which are found in association with Bruch membrane in AMD. Moreover, in vitro studies in human RPE cell line, ARPE-19, revealed that exposure to oxidants resulted in four well known senescence markers, including hypertrophy, senescence-associated β-galactosidase (SA-β-galactosidase) activity, growth arrest and cell cycle arrest in G1/G0.

As described above, none of the current treatment approaches for AMD address the underlying cellular pathology of the disease. Likewise, AD continues to be a disease without an effective cure. Thus, a continuing need exists for treatments of senescence-related degenerative diseases including AMD and AD.

SUMMARY

Provided herein are pharmaceutical compositions which include a therapeutically effective amount of H-Leu-Leu-OMe Hydrochloride or Hydrobromide, or a functional derivative thereof, wherein the composition can be used for treating a degenerative diseases such as an ocular disease, including retinal degenerative diseases such as age related macular degeneration, Retinitis Pigmentosa, Diabetic Retinopathy, and ocular pathologies such as: familial drusen, glaucoma, Stargardt's and Best disease or a degenerative disease such as Alzheimer's Disease (AD) in the subject.

Also provided are methods of treating one of the forgoing diseases and conditions, including the retinal degenerative diseases in a subject by administering to the subject a therapeutically effective amount of an agent, such as H-Leu-Leu-OMe Hydrochloride or Hydrobromide, or a functional derivative thereof.

The foregoing and other objects, features, and advantages will become more apparent from the following detailed description, which proceeds with reference to the accompanying figures.

BRIEF DESCRIPTION OF THE DRAWINGS

FIGS. 1A-1D show that TAK1 is involved in apoptosis and cell-cycle arrest at G0/G1 in RPE cells. FIG. 1A are plotted results from a FACS analysis of a double-staining (annexin and propidium iodide (PI)) assay of RPE cells that were untreated (left), treated with $H_2O_2$ (center), or treated with $H_2O_2$ and the TAK1 inhibitor 5Z-7-oxozeaenol (right). FIG. 1B shows FACS analysis and of RPE cells pretreated with the TAK1 inhibitor with or without $H_2O_2$ as described in A. The percentage of cells in each cell-cycle phase (G1/G0, S, and G2/M) was determined by its DNA content (FL2A), as reflected on the x-axis. FIG. 1C presents the results of the FACS analysis of FIG. 1B in table form. FIG. 1D is a chart illustrating the results of a XTT assay comparing viability of ARPE-19 cells pretreated with the TAK1 inhibitor 5Z-7-oxozeaenol (1 µM) or left untreated for 1 hour.

FIG. 2A are representative photographs showing SA-β-gal staining of RPE cells treated at the indicated times with TAK1 inhibitor 5Z-7-oxozeaenol or left untreated. FIG. 2B is a histogram representing the relative amounts of cells that were stained positively with SA-β-gal (% of cells/field) in inhibitor-treated and untreated cells on the indicated days. FIG. 2C are representative photographs showing SA-β-gal staining in RPE cells treated with TAK1 inhibitor for one hour and then treated with 200 µM $H_2O_2$ for 1 hour, or only with $H_2O_2$. FIG. 2D is a histogram showing relative amounts of cells that were stained positively with SA-β-gal (% of cells/field) with $H_2O_2$ alone or with $H_2O_2$ combined with TAK1 inhibitor.

FIG. 3A shows Western blot analysis of RPE cells were treated with the TAK1 inhibitor 5Z-7-oxozeaenol (1 µM) or were left untreated for 1 hour. Separated total protein extracts were analyzed with the indicated antibodies, and normalized to GAPDH. FIG. 3B is a graph presenting phospho-p38 levels normalized to p38. FIG. 3C shows a Western blot analysis of RPE cells left untreated, treated with $H_2O_2$, or were treated with the TAK1 inhibitor 5Z-7-oxozeaenol (1 µM), and then treated with $H_2O_2$, and grown to the indicated days. FIG. 3D is a histogram presenting the results of the Western blot of FIG. 3C. p53 levels were normalized to GAPDH (results are the mean of two independent experiments).

FIG. 6A shows representative photographs of the following conditions (left to right): Untreated RPE cells, mostly negatively for SA-β-gal staining, with normal morphology; RPE cells treated with oxidative stress with or without TAK-1 inhibition (5z-7 oxozeanol), RPE cells positively stained with SA-β-gal with hypertrophy, flattened and abnormal shape of the RPE cells. FIG. 6B shows quantification of the different cells size using Image software. N=40 cells for each treatment.

FIG. 8A shows representative photographs showing SA-β-gal staining of RPE cells treated with different anisomycin concentrations or left untreated, as indicated. FIG. 8B: ARPE-19 cells were seeded in 96-well plates (5000 cells/well) in full medium and were pretreated with the TAK1 inhibitor 5Z-7-oxozeaenol (1 µM), $H_2O_2$, and Anisomycin alone or in combination or left untreated for 1 hour. Their viability was then assayed by the XTT assay. The experiment was performed in triplicate.

FIG. 9A: Total protein extracts were separated by SDS-PAGE and analyzed with the indicated antibodies. FIG. 9B: The histogram represents the activity of TAK1 manifested by increase in the phosphorylation TAK1 substrate p38.

DETAILED DESCRIPTION

I. Abbreviations

Figure 1A:
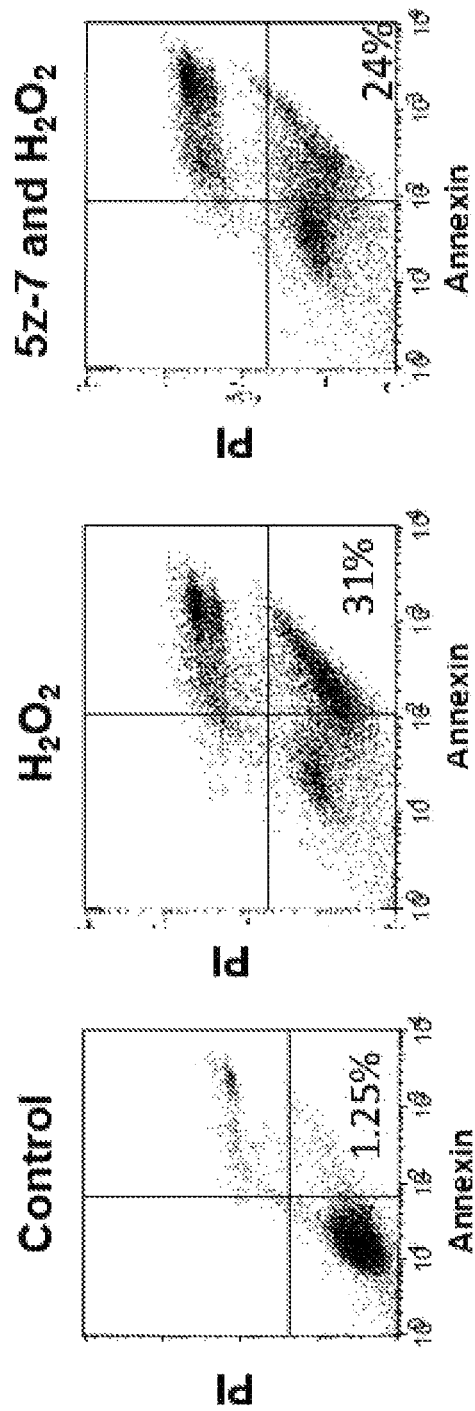

AMD Age-related macular degeneration
LLMe H-Leu-Leu-OMe Hydrochloride
RPE Retinal pigment epithelium
TAK1 Transforming growth factor-beta activated kinase 1

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Abnormal: Deviation from normal characteristics. Normal characteristics can be found in a control, a standard for a population, etc. For instance, where the abnormal condition is a disease condition, such as a retinal degenerative disease, a few appropriate sources of normal characteristics might include an individual who is not suffering from the disease (e.g., dry AMD), a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as reduced central vision) can be described as being associated with the biological condition of early AMD and tendency to develop advanced AMD and complete vision loss.

Administration: The introduction of a composition, such as an agent that activates p38 and/or JNK signaling via TAK1 activation, into a subject by a chosen route. Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intraocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as biocompatible intraocular implants, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19*th Edition* (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances. As used herein, a "functional derivative" of an agent, such as anisomycin or H-Leu-Leu-OMe Hydrochloride, includes, analogs, derivatives, and mimetics of the agent that share the biological activity of the native (non-derived) molecule.

Antibody: A polypeptide ligand comprising at least a light chain or heavy chain immunoglobulin variable region, which specifically recognizes and binds an epitope of an antigen, such as TAK1, p38 or JNK protein or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, immunology, 3rd Ed., W.H. Freeman & Co., New York, 1997. In particular embodiments of the compositions and methods described herein, the active agent is an activating antibody that increases an activity of p38 and/or JNK signaling. Antibodies may function as mimics of a target protein activity, or as blockers of the target protein activity, with therapeutic effect derived therein.

Cellular senescence: Refers to the essentially irreversible growth arrest that occurs when cells that can propagate stop dividing, and is often referred to as just "senescence." Cellular senescence was formerly described as a process that reduces the proliferation (growth) of normal human cells in culture[4]. There are numerous senescence-inducing stimuli. It was demonstrated that the limited growth of human cells in culture is due in part to telomere erosion—the gradual loss of DNA at the ends of chromosomes (4). Furthermore, many senescent cells harbor genomic damage at non-telomeric sites, which also generate the persistence of DNA damage signaling needed for the senescence growth arrest. DNA double strand breaks are especially potent senescence inducers. The senescence growth arrest is not simply a halt in cell proliferation. Senescent cells show marked and distinct changes in their pattern of gene expression (5). Though a relatively new concept, RPE cellular senescence is considered a risk factor in the onset and progression of AMD (6).

Diagnosis: The process of identifying a disease or a predisposition to developing a disease, for example, a retinal degenerative disease, by its signs, symptoms, and results of various tests and methods. The conclusion reached through that process is also called "a diagnosis." Forms of optical testing commonly performed include but are not limited to physical examinations, visual field, imaging such as optical coherence tomography (OCT), and physiological tests such as electroretinography. The term "predisposition" refers to an effect of a factor or factors that render a subject susceptible to a condition, disease, or disorder, such as a retinal degenerative disease, such as a particular genetic mutation. In some examples, of the disclosed methods, testing is able to identify a subject predisposed to developing a condition, disease, or disorder, such as AMD.

Efficacy: Refers to the ability of agent to elicit a desired therapeutic effect. Efficacy also refers to the strength or effectiveness of a compound. As used herein, "enhancing efficacy" means to increase the therapeutic action of an agent.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Functional fragments and variants of a polypeptide: Included are those fragments and variants that maintain one or more functions of the parent polypeptide, including natural isoforms resultant from alternative splicing or transcription events. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Mitogen-activated protein kinase signaling: MAPK kinase signaling is involved in cellular events such as growth, differentiation and stress responses (7). Four parallel MAPK pathways have been identified to date: ERK1/ERK2, JNK, p38 and ERK5 (8). These pathways are linear kinase cascades in that MAPKKK phosphorylates and activates MAPKK, and MAPKK phosphorylates and activates MAPK. Activation of these pathways regulates the activity of a number of substrates through phosphorylation. MAPK signaling cascades are involved in controlling cellular processes including proliferation, differentiation, apoptosis, and stress responses Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Preventing or treating a disease: Preventing a disease refers to inhibiting the onset or the full development of a disease, for example inhibiting the development of complete vision loss in a person who has early dry AMD. Treatment refers to a therapeutic intervention that ameliorates a sign or symptom of a disease or pathological condition after it has begun to develop.

Retinal degenerative disease: A disease caused by deterioration of the retina, commonly associated with progressive vision loss, and particularly photoreceptor deterioration. Retinal degeneration can result from multiple causes. In particular embodiments, senescence, leading to atrophy of retinal pigment epithelium (RPE) cells can lead to photoreceptor loss. The RPE is the layer of cells that servers to protect and provide nutrition to photoreceptors. In particular retinal degenerative diseases such as but not limited to dry AMD, wet AMD, diabetic retinopathy, and retinitis pigmentosa, it is RPE dysfunction that results in progressive photoreceptor loss.

Small molecule: A molecule, typically with a molecular weight less than 1000, or in some embodiments, less than about 500 Daltons.

Subject: Living multi-cellular organisms, including vertebrate organisms, a category that includes both human and non-human mammals.

Subject susceptible to a disease or condition: A subject capable of, prone to, or predisposed to developing a disease or condition. It is understood that a subject already having or showing symptoms of a disease or condition is considered "susceptible" since they have already developed it.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Transforming growth factor-beta activated kinase 1 (TAK1): TAK1 is a member of the MAPKKK family, and was first reported as a regulator of MAP kinase signaling induced by TGF-β or oxidative stress (9). TAK1 is known to be activated by stress signals as well as proinflammatory cytokines, and is involved in activation of p38 and JNK signaling. TAK1 was originally known as MAP3K7.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

III. Overview of Several Embodiments

Provided herein are pharmaceutical compositions containing a therapeutically effective amount of H-Leu-Leu-OMe Hydrochloride (LLMe), or a functional derivative thereof, for use in treating a retinal degenerative disease as described herein including ocular disease, including diseases such as age related macular degeneration, Retinitis Pigmentosa, Diabetic Retinopathy, and ocular pathologies such as: familial drusen, glaucoma, Stargardt's and Best disease or a degenerative disease such as Alzheimer's Disease (AD) in the subject. or Alzheimer's Disease (AD) in a subject.

In particular embodiments the described compositions are for treatment of a retinal degenerative disease selected from the group consisting of dry age-related macular degeneration (AMD), wet AMD, diabetic retinopathy, and retinitis pigmentosa.

In other embodiments the described pharmaceutical compositions also contain an additional agent for treatment of the retinal degenerative disease or Alzheimer's disease, such as an additional agent is selected from the group consisting of a transforming growth factor-beta activated kinase 1 (TAK1), a TAK1 binding protein (TBP1), and a small molecule. In particular examples, the small molecule is anisomycin or functional derivative thereof.

In some embodiments, the described pharmaceutical compositions are formulated for injection into the ocular space of the subject, as an ocular ointment, or as eye drops. In other embodiments, the pharmaceutical composition is incorporated into an ocular implant.

Also provided herein are methods using the described compositions, including methods for treating a retinal degenerative disease as described herein, or Alzheimer's Disease in a subject by administering to the subject a therapeutically effective amount of a pharmaceutical composition comprising a H-Leu-Leu-OMe Hydrochloride (LLMe), or a functional derivative thereof.

In particular embodiments, the methods are for treatment of a retinal degenerative disease selected from the group consisting of dry age-related macular degeneration (AMD), wet AMD, diabetic retinopathy, and retinitis pigmentosa.

In other embodiments, the methods also involve administering to the subject an additional agent for treatment of the retinal degenerative disease or Alzheimer's Disease, including an agent is selected from the group consisting of a transforming growth factor-beta activated kinase 1 (TAK1), a TAK1 binding protein (TBP1), and a small molecule, such as anisomycin or a functional derivative thereof.

In particular embodiments of the described methods, the pharmaceutical composition is formulated for injection into the ocular space of the subject, as an ocular ointment, or as eye drops. In other embodiments, the pharmaceutical composition is incorporated into an ocular implant.

IV. Compositions for Treatment or Prevention of Degenerative Disease Including Retinal Degeneration Described herein is the finding that inhibition of TAK1 MAP kinase, which is involved in activation of the p38 and JNK signaling pathways, promotes senescence and atrophy of retinal pigment epithelial (RPE) cells. Conversely, it has also been discovered that TAK1 stimulation, for example, by the small molecule anisomycin, or treatment of RPE cells with H-Leu-Leu-OMe Hydrochloride (LLMe), inhibits RPE senescence. RPE dysfunction is a key factor of multiple retinal degenerative diseases, including age related macular degeneration (AMD), diabetic retinopathy, and retinitis pigmentosa (RP). RPE dysfunction is also a resulting consequence of pathologies associated with intravitreal injection and intravitreal implantation.

Accordingly, provided herein are compositions for use and methods of treatment and prevention for retinal degenerative diseases. The compositions and methods that include use of an active agent that promotes p38 and/or JNK signaling via upstream activation of TAK1 in RPE cells, such as a small molecule, peptide, or antibody.

In particular embodiments, the small molecule is anisomycin, or a functional derivative thereof.

Anisomycin ((2R,3S,4S)-4-hydroxy-2-(4-methoxybenzyl)-pyrrolidin-3-yl acetate; also known as flagecidin) is a translational inhibitor secreted by *Streptomyces* spp., and strongly activates the stress-activated mitogen-activated protein (MAP) kinases and p38/RK in mammalian cells, resulting in rapid induction of immediate early genes in the pathway. The structure of anisomycin is shown as Formula I:

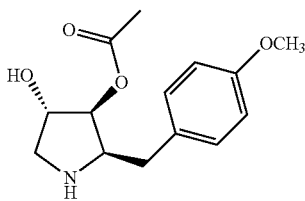 [SMILES: COc1ccc(C[C@H]2NC[C@H](O)[C@H]2OC(C)=O)cc1]

Additionally provided herein are pharmaceutical compositions, and methods of their use, for treating a retinal degenerative disease or Alzheimer's disease, which include an effective amount of the small molecule H-Leu-Leu-OMe Hydrochloride (LLMe), or functional derivative thereof. The structure of LLme is shown as Formula II:

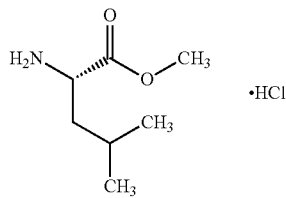

In other embodiments, it is the hydrobromide form of LLme that is used.

In particular embodiments, the agent for stimulation of TAK1, p38 and/or JNK signaling in RPE cells is an activating peptide of the signaling pathways. Multiple peptides are known to activate the p38 and JNK signaling pathways, including but not limited to one of the TAK1 isoforms, TAB1, MKK3/4/6, MLK1, ASK1, and MEKK1, which are commercially available. In particular embodiments, the peptide is formulated for direct administration to the intraocular space of a subject. In other embodiments, the active peptide is expressed from a nucleic acid vector which itself is provided to the intraocular space of the subject. Methods of recombination protein expression (including construction of a protein expressing construct based upon a peptide sequence) are commonly known in the art and are encompassed by this disclosure. It is also appreciated that functional variants of a p38 and/or JNK stimulating protein can be produced by standard methods of mutagenesis, which will maintain the activity of the wild type protein, and can be used in the compositions and methods described herein. Such functional variants can be identical in sequence to the wild type peptides by at least 98%, at least 95%, at least 90%, at least 85%, at least 80%, or even less than 80% sequence identity. It is appreciated that TAK1 was formerly called MAP3K7, and that several TAK1 isoforms exist, and this disclosure encompasses all isoforms and variants of TAK1/MAP3K7 that share p38/JNK activating catalytic activity.

In other embodiments, the p38 and/or JNK stimulating agent is an activating antibody that binds to an activating cellular receptor upstream in the p38 and/or JNK signaling pathways. In a particular example, the activating antibody specifically recognizes, binds to, and activates the TGFβ receptor 1. In other examples a TAK1-activating antibody binds to one of the multiple stress-responsive receptors upstream of TAK1 activation (eg. a member of the Toll-like Receptor (TLR) family).

The TAK1, p38 and/or JNK pathway stimulating agents described herein can be used in pharmaceutical compositions as described herein for treatment and or prevention of retinal degenerative diseases. In methods of using the described agents, a therapeutically effective amount of an agent is administered to a subject in need of such treatment. Such subjects include, patients diagnosed or predisposed to the retinal disease.

In particular examples, the subject has been diagnosed with the disease (e.g. by detection of retinal drusen; mild vision loss; loss of visual field; abnormal retinal thickness, as determined by OCT imaging; and decreased photoreceptor activity as determined by abnormal ERG results). In such examples, administration of a composition including an agent described herein can slow or halt the progression of the disease. For example, a subject diagnosed with early dry AMD who is treated could have no further degradation in visual ability and would not advance to the late stage of the disease.

In other examples, the methods described herein can be used to prevent development of a retinal degenerative disease in a subject who is predisposed to that disease. Such predisposition can be determined for example by detection of a genetic mutation associated with retinal dysfunction. Administration of an active agent described herein, and which prevents retinal degradation can thus be understood to prevent development of the disease.

Combination Therapies

In particular embodiments of the compositions and methods described herein, the LLMe-containing composition is combined with an agent which stimulates TAK1, p38 and/or JNK signaling, or upstream MAP kinase as described herein, or is also combined with at least one additional active agent to treat or prevent retinal degeneration.

In some embodiments, the combination is administered to a subject in a single composition. In particular examples, the combination compositions are formulated so that the component active ingredients are simultaneously available in the subject in an active form. In other examples, the component active ingredients are formulated such that the components are sequentially available in an active form to the subject.

In other embodiments, the combinations LLMe and an agent which stimulates p38 and/or JNK signaling via TAK1 activation or at least one additional active agent to treat or prevent retinal degeneration can be administered to a subject in multiple compositions, one containing, for example, LLMe, and at least one additional composition containing the at least one additional active agent. The timing and order of administration of such multiple compositions can vary. In particular examples, the compositions are provided simultaneously, but in other examples they are provided one before or after the other. It is contemplated that when administered at separate times, significant time may elapse between administration of the at least two compositions, such as several hours, several days or even longer.

Pharmaceutical Compositions and Modes of Administration

It is contemplated that the pharmaceutical agents for use in the described treatments can be supplied in any pharmaceutically acceptable compositions.

Among the pharmaceutical compositions specifically contemplated in the present disclosure are pharmaceutically acceptable acid or base addition salts of small molecules such as, but not limited to Anisomycin D or LLMe. The phrase "pharmaceutically acceptable acid or base addition salts" includes therapeutically active non-toxic acid and non-toxic base addition salt forms which Anisomycin D or LLMe is able to form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Small molecules such as, but not limited to anisomycin which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms small molecules such as, but not limited to anisomycin, are able to form. Examples of such forms are, for instance, hydrates, alcoholates and the like.

Also contemplated for use in methods and compositions described herein are sterochemcially isomeric forms of small molecules such as, but not limited to Anisomycin D or LLMe. The term stereochemically isomeric form includes all possible compounds made up of the same atoms bonded by the same sequence of bonds, but having different three-dimensional structures that are not interchangeable. Unless otherwise mentioned or indicated, the chemical designation of a compound encompasses the mixture of all possible stereochemically isomeric forms that the compound may possess. Such mixture may contain all diastereomers and/or enantiomers of the basic molecular structure of the compound. Also contemplated are all stereochemically isomeric forms in pure form or in admixture with each other.

Various delivery systems are known and can be used to administer the peptides, antibodies, and small molecules described herein. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid (expressing the described peptide or antibody) as part of a retroviral or other vector, and the like. Methods of introduction include, but are not limited to, intraocular, intrathecal, intradermal, intramuscular, intraperitoneal (ip), intravenous (iv), subcutaneous, intranasal, epidural, and oral routes. The therapeutics may be administered by any convenient route, including, for example, infusion or bolus injection, topical, absorption through epithelial or mucocutaneous linings (e.g., oral mucosa, rectal and intestinal mucosa, and the like) ophthalmic, nasal, and transdermal routes, and may be administered together with other biologically active agents.

In a specific embodiment, it may be desirable to administer the described pharmaceutical treatments by injection, catheter, suppository, or implant (e.g., implants formed from porous, non-porous, or gelatinous materials, including membranes, such as sialastic membranes or fibers), and the like. In another embodiment, therapeutic agents are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, any one of the agents used in the combination treatments can be delivered in a controlled release system. In one embodiment, a pump may be used (see, e.g., Langer *Science* 249, 1527, 1990; Sefton Crit. *Rev. Biomed. Eng.* 14, 201, 1987; Buchwald et al., *Surgery* 88, 507, 1980; Saudek et al., *N. Engl. J. Med.* 321, 574, 1989). In another embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

In particular examples where combination treatments are used, LLMe and agents that stimulate p38 and/or JNK signaling, or at least one additional agent from treatment of retinal degeneration are administered simultaneously, and by the same mode of administration. In other examples, the pharmaceutical compounds are administered at different times, and either by the same or different more of administration.

The vehicle in which the agent is delivered can include pharmaceutically acceptable compositions of the compounds, using methods well known to those with skill in the art. For instance, in some embodiments, the agents described herein are typically contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The combination treatments of this disclosure can be formulated in accordance with routine procedures as pharmaceutical compositions adapted for intravenous administration to human beings. Typically, compositions for intravenous administration are solutions in sterile isotonic aqueous buffer. Where necessary, the compositions may also include a solubilizing agent and a local anesthetic such as lidocaine to ease pain at the site of the injection.

The ingredients in various embodiments are supplied either separately or mixed together in unit dosage form, for example, in solid, semi-solid and liquid dosage forms such as tablets, pills, powders, liquid solutions, including eye drops, ointments, or suspensions, or as a dry lyophilized powder or water free concentrate in a hermetically sealed container such as an ampoule or sachette indicating the quantity of active agent.

The amount of each therapeutic agent that will be effective will depend on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each patient's circumstances. Exemplary dosages of the individual compounds are described herein, but myriad other dosage regimens are encompassed by this disclosure. An example of an additional dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. In a particular example, anisomycin is administered to a subject at a concentration of less then 10 ng/ml.

The therapeutic compounds and compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

In some embodiments, sustained localized release of the pharmaceutical preparation that comprises a therapeutically effective amount of a therapeutic compound or composition may be beneficial. Slow-release formulations are known to those of ordinary skill in the art. By way of example, polymers such as bis(p-carboxyphenoxy)propane-sebacic-acid or lecithin suspensions may be used to provide sustained localized release.

It is specifically contemplated in some embodiments that delivery is via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

The following examples are provided to illustrate certain particular features and/or embodiments. These examples should not be construed to limit the disclosure to the particular features or embodiments described.

EXAMPLES

Example 1: TAK1 Inhibition Increases Senescence of Retinal Pigment Epithelial Cells This example shows that inhibition of the TAK1 MAP kinase promotes senescence of retinal pigment epithelial (RPE) cells.

Methods

Double-staining (annexin and propidium iodide (PI)) assay of RPE cells. RPE cells (ARPE-19, available from ATCC) were treated for one hour with the TAK1 inhibitor {5Z-7-oxozeaenol (1 µM)}, following 200 µM $H_2O_2$ for one hour or left untreated. The cells were then washed with fresh medium and after 24 hours were trypsinized, stained, and analyzed by FACS. The percentage of cells in each cell-cycle phase (G1/G0, S, and G2/M) was determined by its DNA content (FL2A).

Cell viability assays ARPE-19 cells were seeded in 96-well plates (5000 cells/well) in full medium and were pretreated with the TAK1 inhibitor 5Z-7-oxozeaenol (1 µM) or left untreated for 1 hour. Their viability was then assayed by the XTT assay (cell proliferation kit cat #20-300-1000; Beit Haemek, Israel).

SA-β-gal staining was carried out as described (10).

Western blot analysis was performed by standard protocols (11), p53, p38, phospho-p38, GADPH, and TAK1; antibodies were obtained from Enco, Israel.

Results

The role of TAK1 in the inflammatory response is characterized (12, 13), but little is known about its participation in the response of RPE cells to stress. RPE cells were treated with the TAK1 inhibitor 5Z-7-oxozeaenol (1 µM) for 1 hour before further treatment with $H_2O_2$ (200 µM). Staining with annexin and propidium iodide and FACS analysis showed that compared to untreated RPE cells, in which the number of apoptotic cells expressed as a percentage of the total number was 1.25%, the number of apoptotic cells after treatment with $H_2O_2$ alone increased over the same time period to 31%. In contrast, in cells treated with the TAK1 inhibitor prior to their treatment with $H_2O_2$ the number apoptotic cells was 24% (FIG. 1A). The number of cells in the late apoptosis section of each FACS chart (annexin and Pi, upper right panel) was similar with or without TAK1 inhibitor. These results imply that TAK1 is involved in apoptosis and that its inhibition reduces this process.

To examine the effect of TAK1 inhibition on the RPE cell cycle, RPE cells were treated with TAK1 inhibitor, with or without $H_2O_2$. The RPE cells are quiescent and mostly located at the G0/G1 stage (FIGS. 1B and 1C), however, following TAK1 inhibition the percentage of cells at the G0/G1 stage increased to 89% of the total number. When the cells were subjected to oxidative stress ($H_2O_2$ treatment) they exhibit high levels of G2/M arrest. This phenomenon was reduced upon TAK1 inhibition prior to the oxidative stress (FIGS. 1B and C). The Cell cycle arrest at G0/G1 upon TAK1-inhibition was further supported by the reduction in proliferation of RPE cells observed in the presence of the TAK1 inhibitor (FIG. 1D). Untreated cells showed a high rate of proliferation as reflected by their increasing optical density (O.D.), which reached a peak on day 4 in contrast to TAK1 inhibited cells which demonstrated a slower proliferation rate that began to decrease after 3 days (FIG. 1D). These findings suggested that inhibition of TAK1 promotes cell cycle arrest and RPE-cell senescence.

Figure 2A:
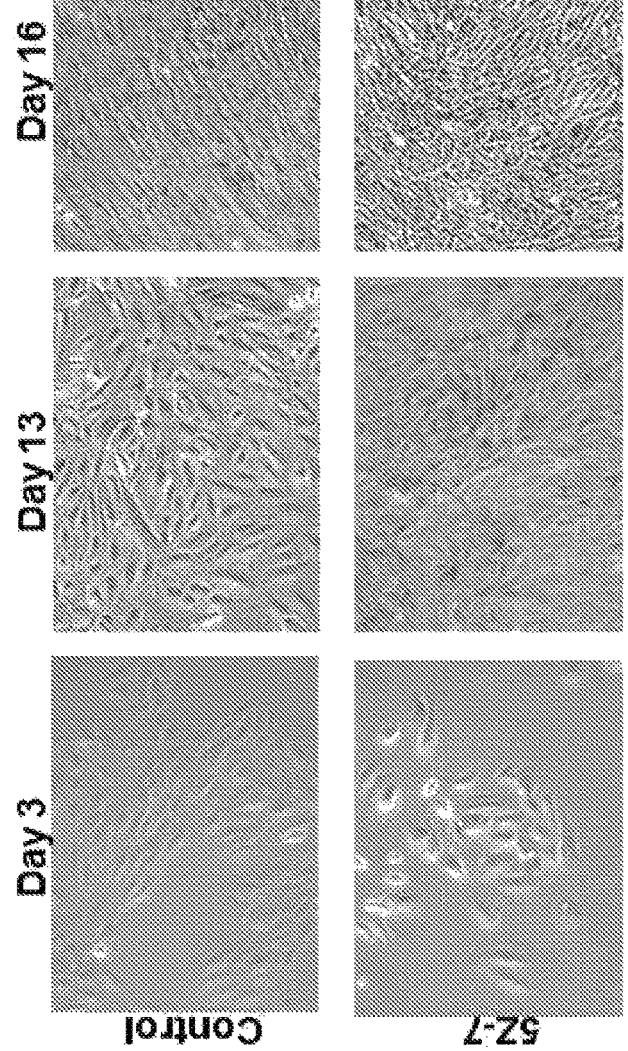
FIGS. 2A-2D show that TAK1 inhibition increases SA-β-gal expression (senescence marker) in RPE cells subjected to oxidative stress.
Figure 2B:
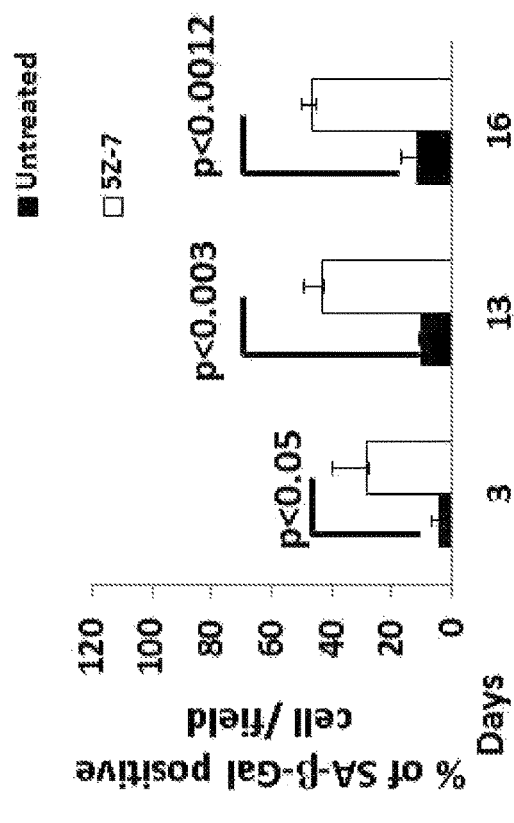
Figure 2C:
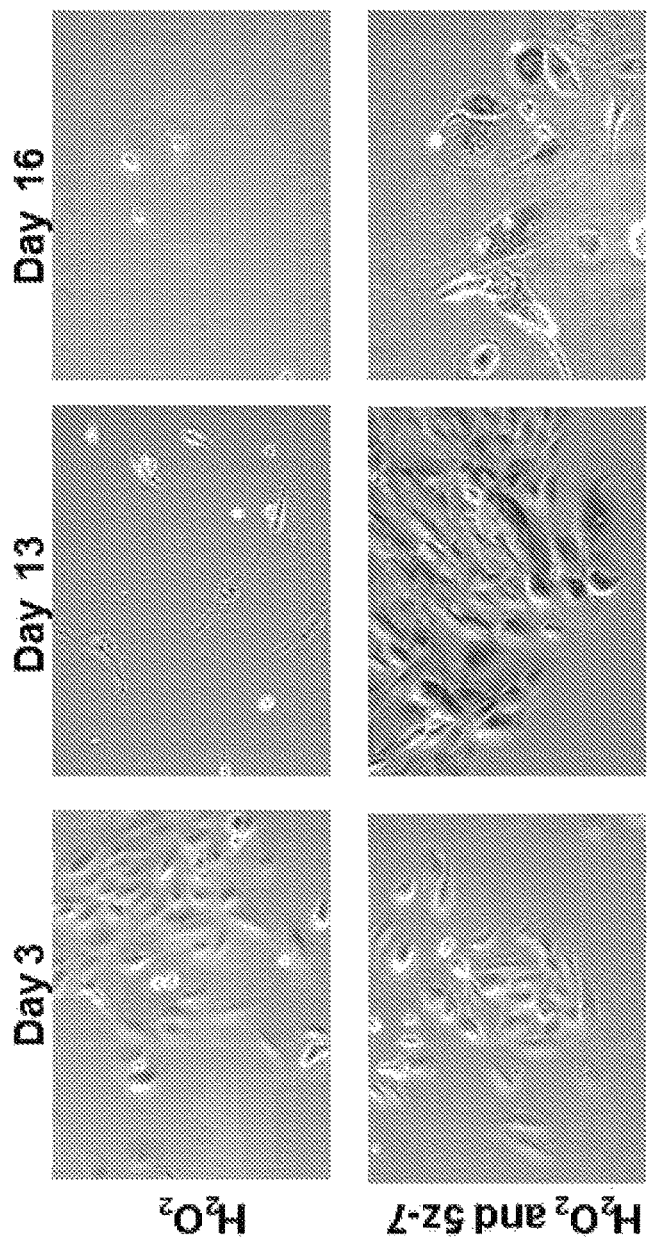
Figure 2D:
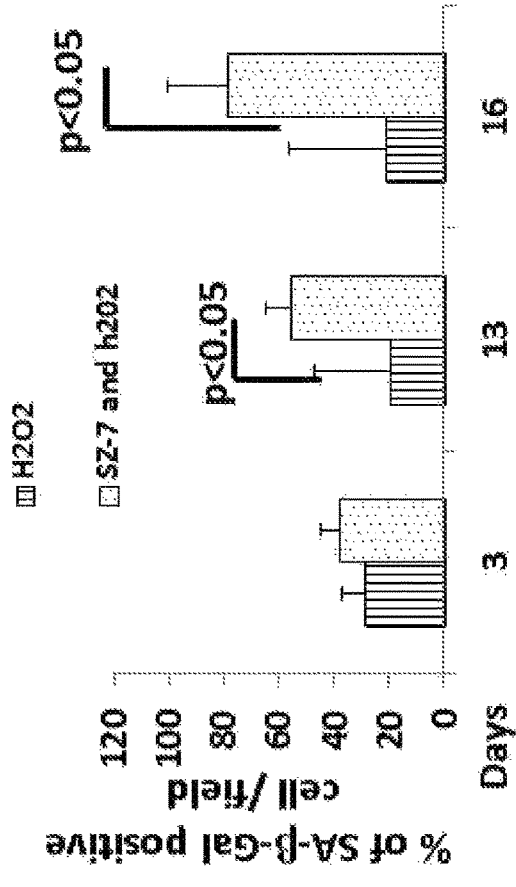

To further characterize the effect of TAK1 inhibition on the senescence of RPE cells, the effect of such inhibition on SA (senescence associated)-β-gal expression was examined in these cells (10). The number of cells expressing SA-β-gal dramatically increased after treatment with the TAK1 inhibitor relative to the number in untreated cells (FIGS. 2A and 2B). This increase was further enhanced when TAK1 was inhibited and the RPE cells were additionally exposed to oxidative stress (FIGS. 2C and 2D). In cells that were exposed to oxidative stress without such pretreatment there was extensive cell death, and by day 16 there were only a few surviving cells, with very low expression of SA-β-gal. In contrast, on days 13 and 16 SA-β-gal was strongly increased in cells that had been exposed to oxidative stress, after pretreatment with the TAK1 inhibitor (FIGS. 2C and D). These findings further support the participation of TAK1 in the regulation of senescence in RPE cells.

Figure 3A:
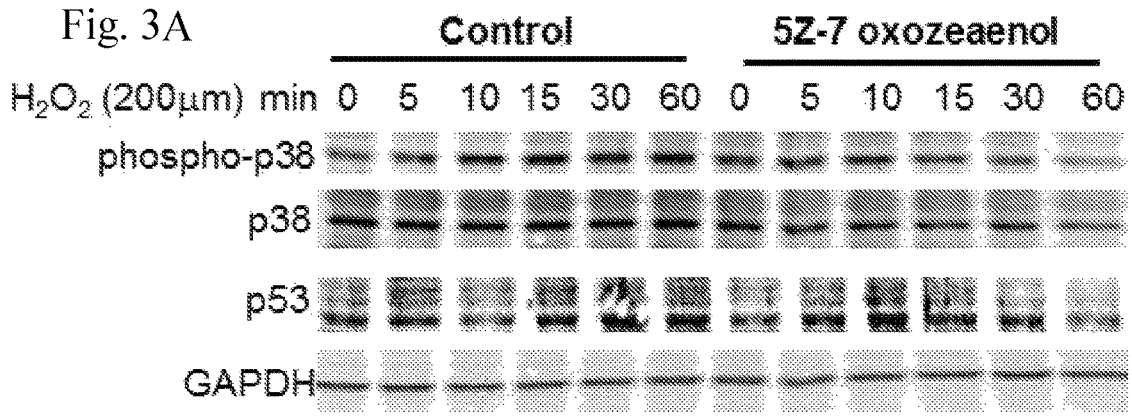
FIGS. 3A-3D show that TAK1 inhibition affects p53 expression during oxidative stress.
Figure 3B:
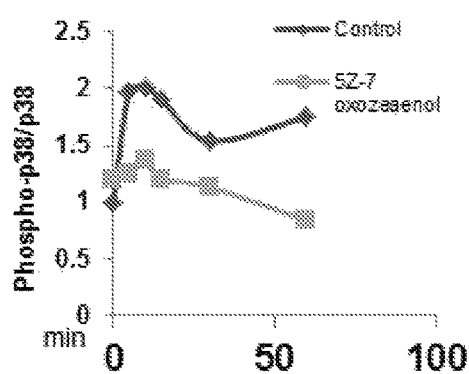
Figure 3C:
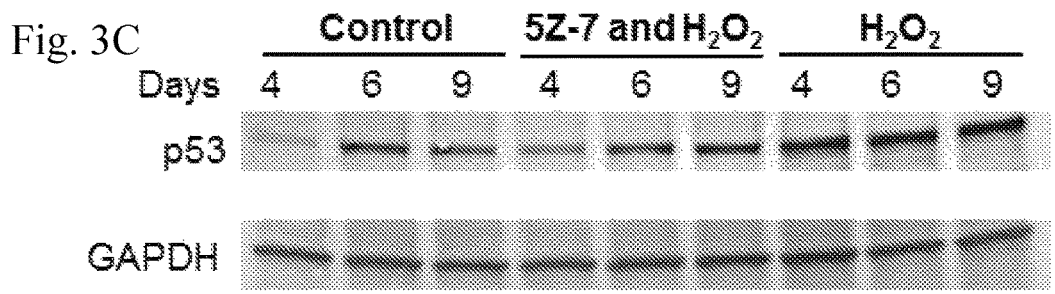
Figure 3D:
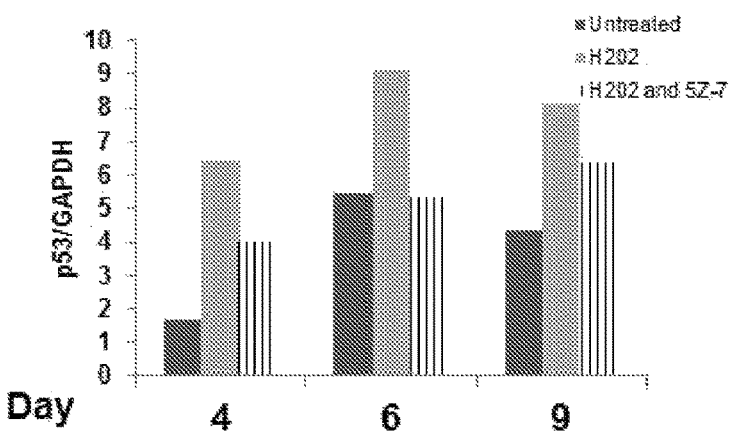

The p53 protein is known to play a critical role in cell-cycle regulation, DNA repair, and programmed cell death (14, 15). In view of this knowledge, and given the above-described observation that TAK1 inhibition reduced apoptosis, the expression of p53 in RPE cells was examined. As shown in FIG. 3A, p53 expression in RPE cells under oxidative stress was strongly affected by pretreatment of the cells with the TAK1 inhibitor, seen by the inhibition of p38 phosphorylation (FIGS. 3A and 3B). In control cells (without such pretreatment) the expression of p53 gradually increased, reaching a peak after 60 min, whereas in the pretreated cells p53 expression peaked after 10 min and then declined (FIG. 3A). Over a longer period, TAK1 inhibition reduced p53 expression levels slightly more than the untreated cells (FIGS. 3C and 3D). In contrast, RPE cells that were exposed to oxidative stress displayed high levels of p53 after 4 days, and its expression gradually increased (FIGS. 3C and 3D).

Figure 4:
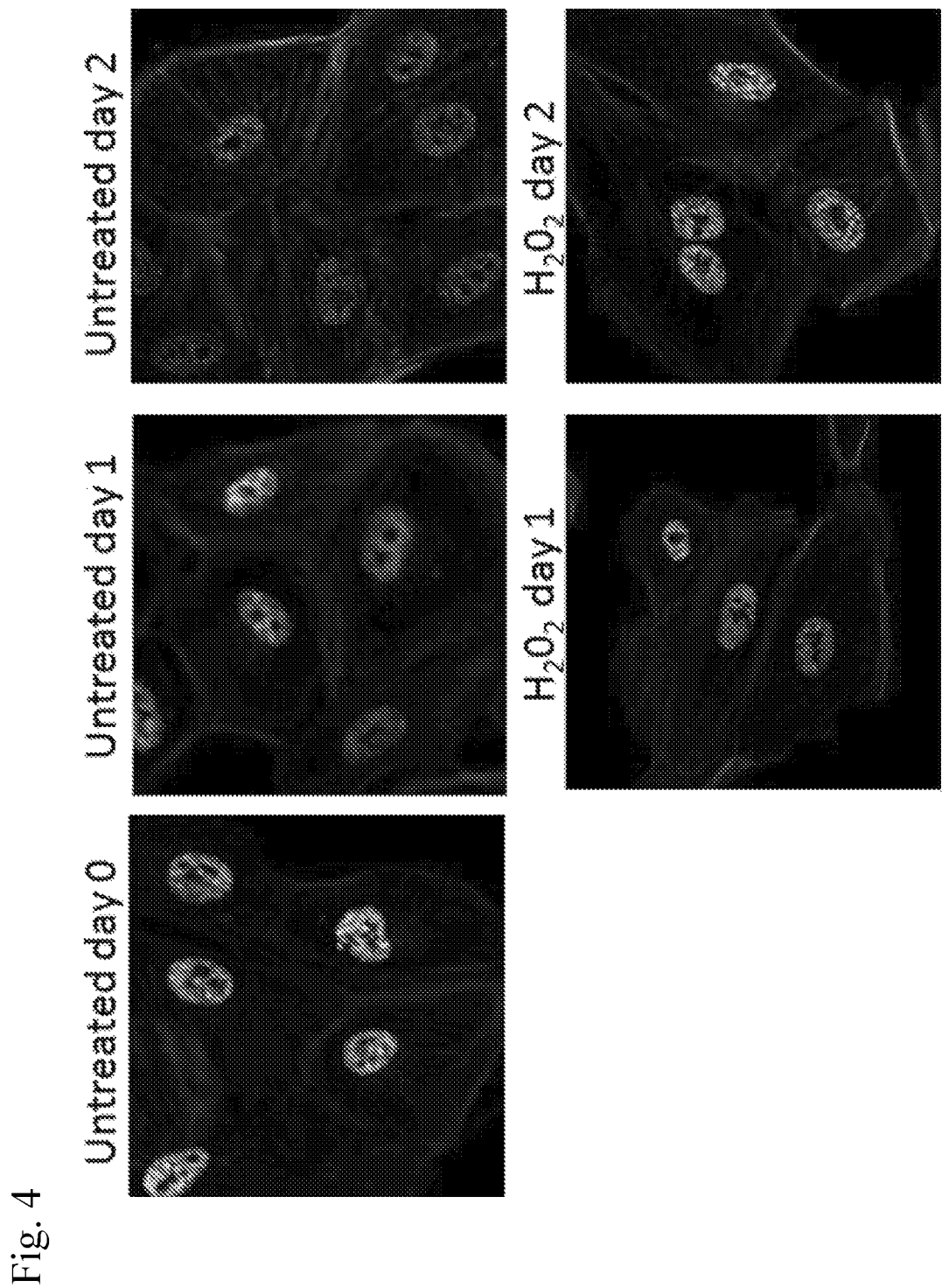
FIG. 4 shows regulation of TAK1 upon oxidative stress. Shown are representative photographs of three independent experiments in which RPE cells were treated with $H_2O_2$ (200 µM, 1 hour) or left untreated. The cells were then immunostained with TAK1 antibodies (green), actin (red) and DAPI (blue).

The extent and expression pattern of TAK1 in the RPE cells were assessed by immunofluorescence. As shown in FIG. 4, TAK1 levels in untreated cells were stable, mainly localized in the nucleus, and with no significant changes observed during the experiments. Interestingly, when the cells were exposed to oxidative stress, TAK1 expression in the nucleus decreased, and returned to normal levels only after 48 hours. This finding implies that TAK1 expression was regulated during oxidative stress, thus demonstrating its importance in this process.

Figure 5:
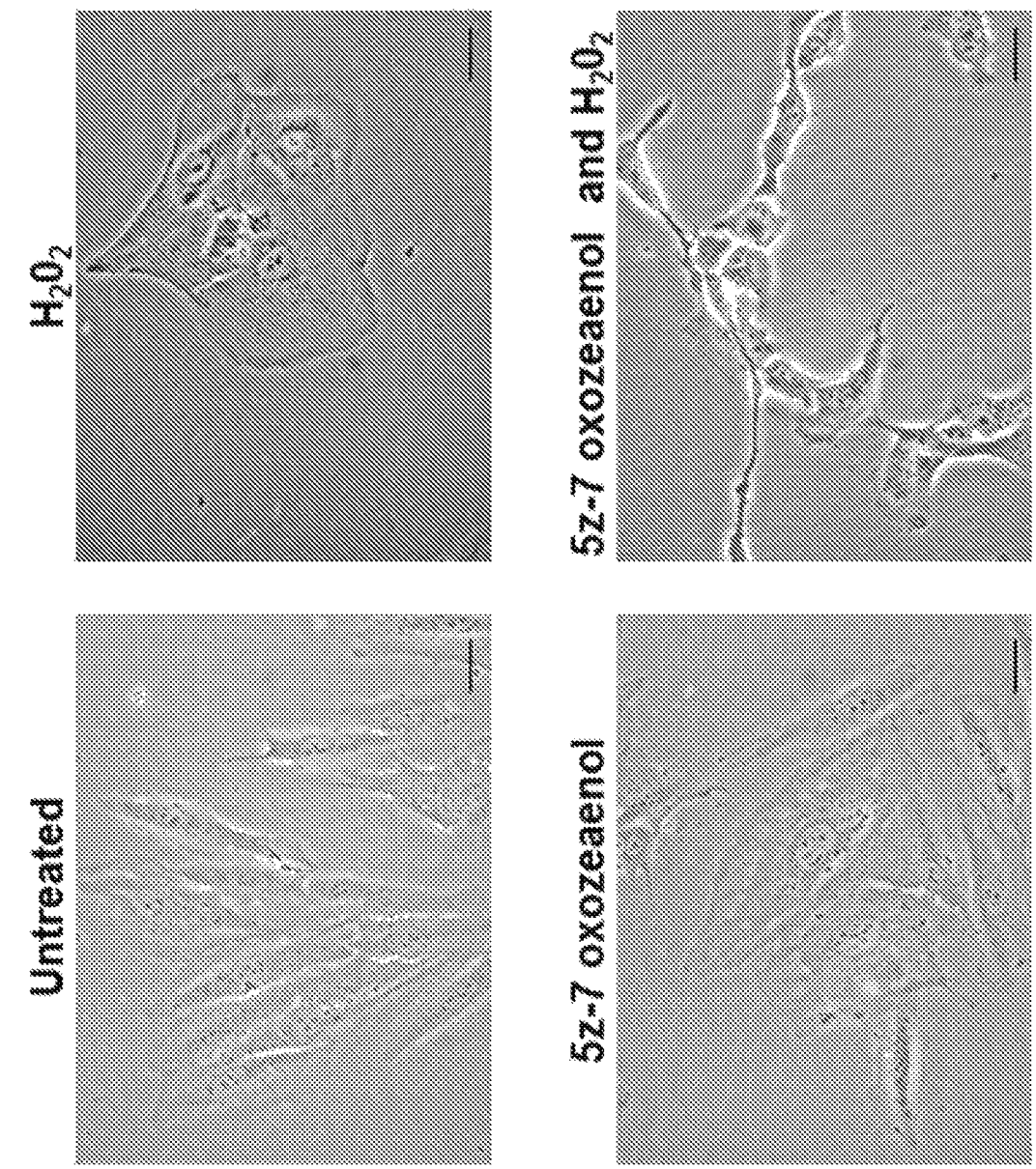
FIG. 5 presents photographs showing that TAK1 inhibition contributes to the SASP of the RPE cells, causing hypertrophy and dysfunction. RPE cells were grown with the TAK1 inhibitor and/or $H_2O_2$ (200 mM) or without treatment. After 2 weeks, conditioned media from the differently treated cells were centrifuge and the supernatants was employed on new freshly cells. Representative photographs of fresh RPE cells treated for 72 hours with the indicated conditioned media are shown. Scale bar=50 µm.

The most significant effect of senescence, is the acquisition of a senescence-associated secretory phenotype (SASP). SASP can convert senescent cells to proinflammatory cells that promote the secretion of chemokines and cytokines that can affect the microenvironment, including in the human retina (16, 17). To examine the role of TAK1 in this process, RPE cells were treated with TAK1 inhibitor or with $H_2O_2$, alone or in combination. After 2 weeks, the media was collected from the three separate treatments, centrifuged and the supernatants (conditioned media) were applied on fresh RPE cells for 72 hours. As shown in FIG. 5, the cells that received conditioned medium from untreated cells displayed a normal phenotype, whereas the cells that received conditioned medium collected from RPE cells treated with either the TAK1 inhibitor or with $H_2O_2$ demonstrated a hypertrophic phenotype similar to that of senescent cells. Interestingly, the cells that received conditioned medium from cells treated with both the TAK1 inhibitor and $H_2O_2$ demonstrated aberrant morphology similar to that of atrophic RPE cells.

Figure 6A:
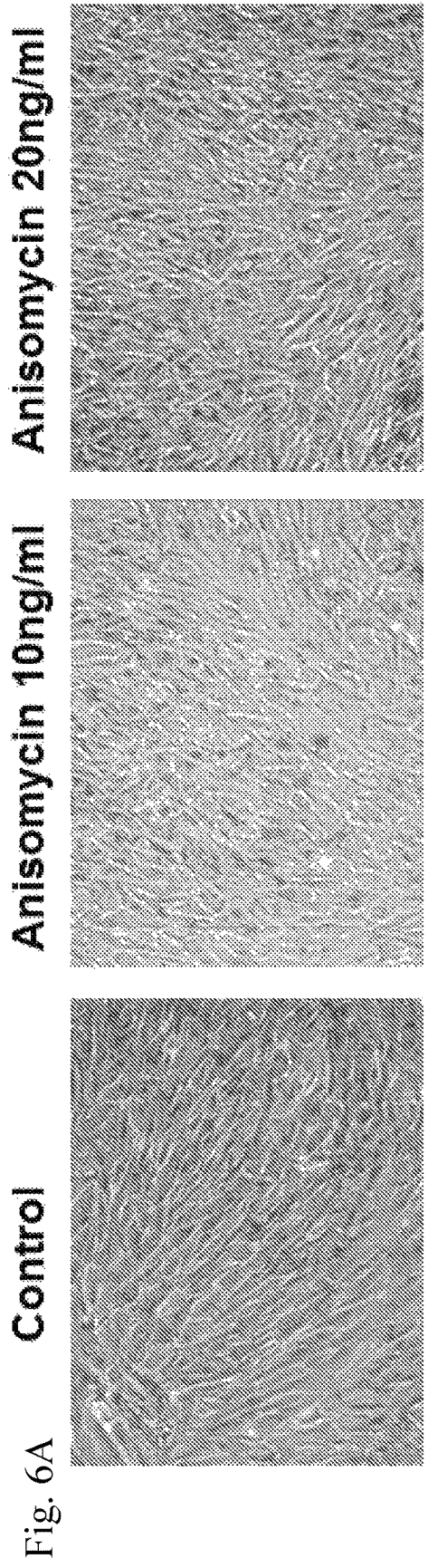
FIGS. 6A-6B show that oxidative stress and TAK1 inhibition increases cell size and SA-β-gal expression in RPE cells.
Figure 6B:
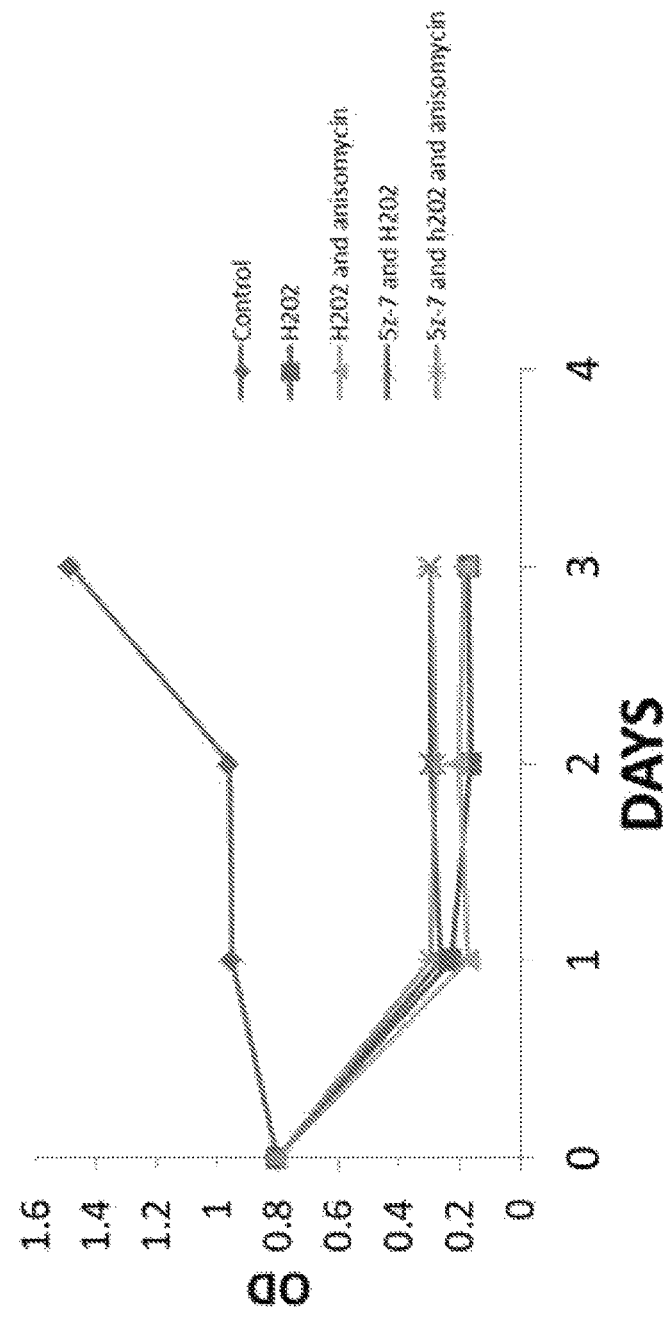

One of the hallmarks of RPE senescence is cellular hypertrophy. RPE cell size is approximately 9-12 μM; but upon oxidative stress or genetic mutation RPE cells can undergo enlargement. As shown in FIG. 6, upon stress, the cells size increase by 4-fold compared to normal cells. However, the combination of TAK1 inhibition with oxidative stress further increases cell size compared to stressed cells (without TAK1 inhibition) and normal cells.

Taken together, these results demonstrate that that TAK1 inhibition promotes RPE cellular senescence, and suggest that agents that promote the TAK1-mediated MAP kinase signaling pathway can be used to inhibit such senescence and by extension, treat RPE-senescence-associated diseases.

Example 2: Treatment with Anisomycin Reduces the Appearance of Senescence in RPE Cells The results presented in Example 1 demonstrate that inhibition of TAK1 signaling promotes RPE cellular senescence. This example shows that anisomycin, a TAK1-signalling promoting agent produces the opposite effect, and reduces RPE cellular senescence.

Methods

All methods are as previously described. Anisomycin was obtained from Sigma Aldrich, Israel.

Results

Figure 7:
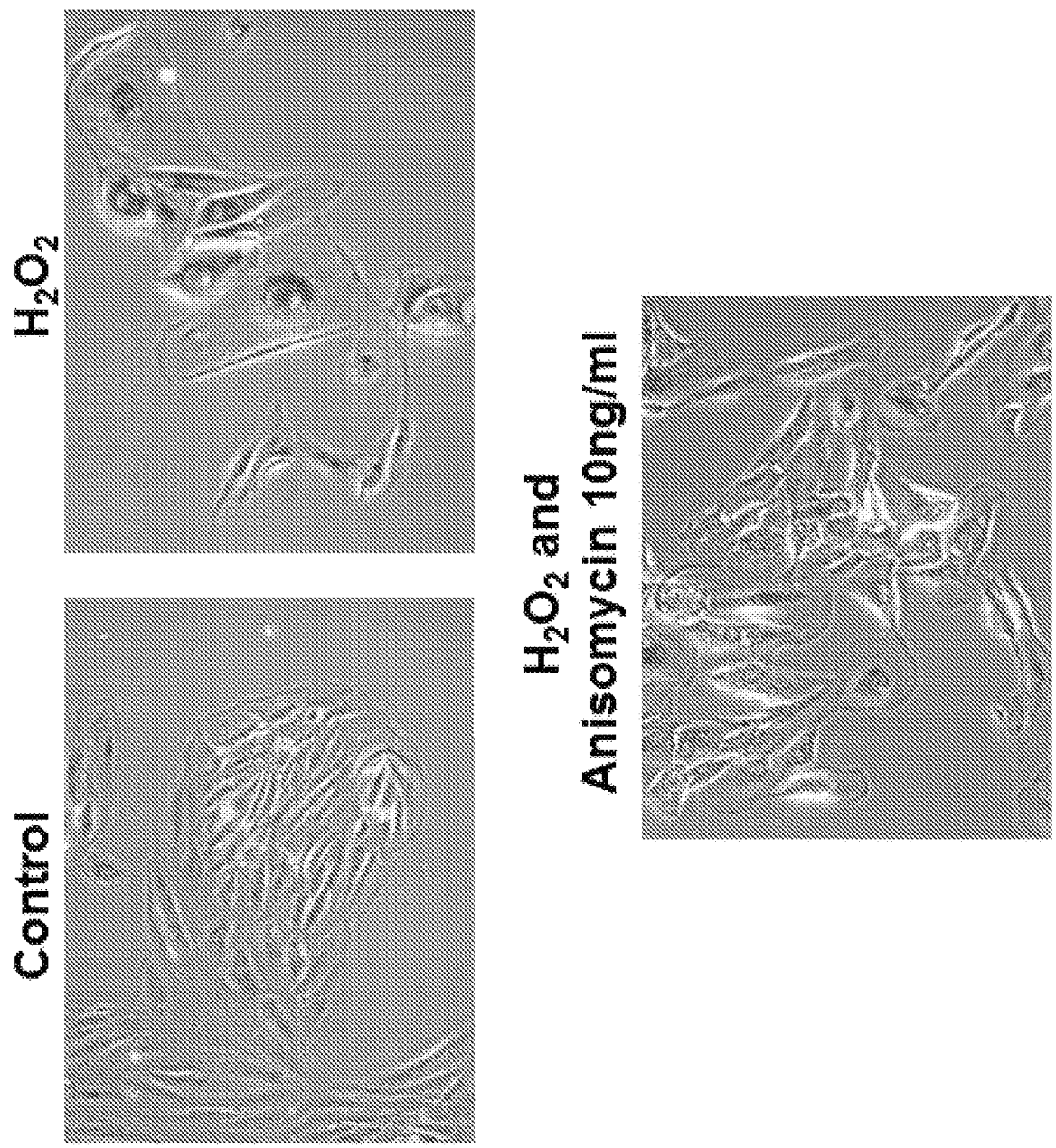
FIG. 7 shows that treatment with anisomycin reduces the appearance of (senescence marker) in RPE cells. REP cells were treated with 200 mM $H_2O_2$ for one hour or left untreated for 10 day. Following treatment (oxidative stress) the cells were treated with or without anisomycin 10 ng/ml for 5 min. Cells were then washed and grown for more than five days. Representative photographs show SA-β-gal staining of control RPE cells, or treated with oxidative stress with or without anisomycin.

Anisomycin was shown to activate kinases associated to the to the MAP kinase such as TAK1. To determine the effects of anisomycin treatment on RPE cells, RPE cells were treated with $H_2O_2$ for 1 hour. Following this treatment, the cells were grown in fresh medium for additional 10 days until appearance of senescence markers. After the tenth day, the cells were treated with anisomycin and grown in fresh medium for an additional five days, stained for the presence of SA-β-Gal, and photographed. Illustrative photographs are shown in FIG. 7. As can be seen in the figure, treatment with anisomycin reduces the number of SA-β-Gal positive cells in comparison to untreated cells exposed to oxidative stress.

Figure 8A:
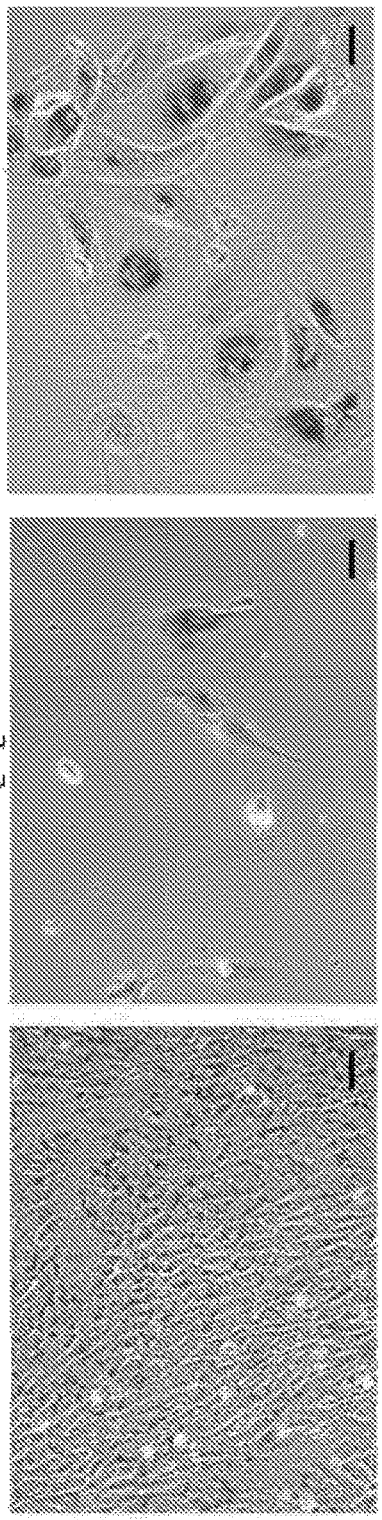
FIGS. 8A-8B illustrate that treatment with anisomycin is not toxic for RPE cells in low concentration.
Figure 8B:
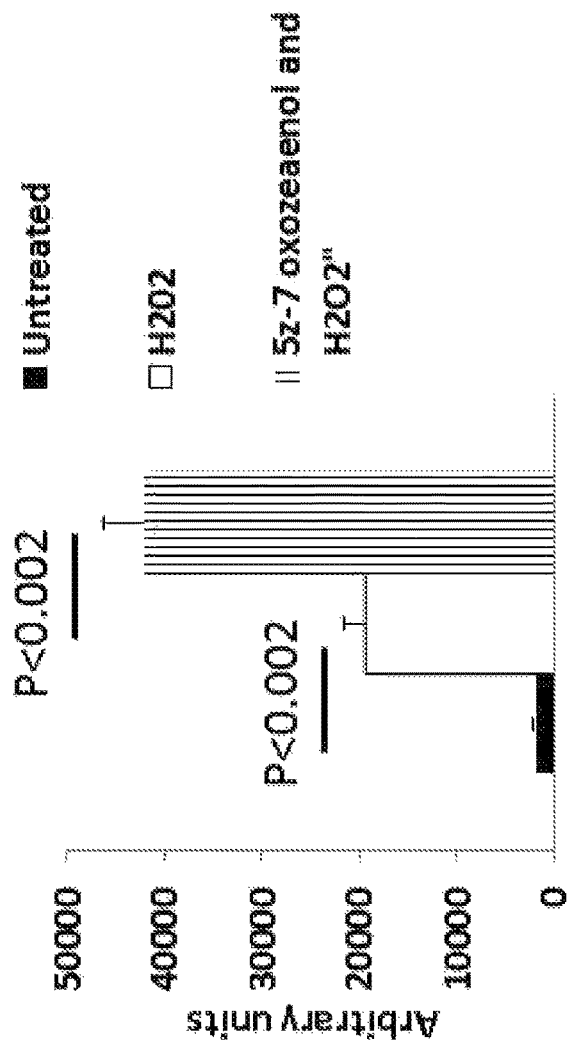

To determine possible toxicity of anisomycin to RPE cells, RPE cells were treated with anisomycin at different concentration for 5 minute periods. Following treatment, the medium was replaced and fresh medium was added. 72 hours post-treatment, the cells were photographed. As can be seen in FIG. 8A cellular morphology was similar to the control cells, thus demonstrating that in low levels anisomycin is not toxic. Furthermore, the rate of cell proliferation with oxidative stress and anisomycin did not display reduction in the rate of cells proliferation. FIG. 8B shows ARPE-19 cells that were pretreated with the TAK1 inhibitor 5Z-7-oxozeaenol (1 µM), $H_2O_2$, and anisomycin alone or in combination, or left untreated for 1 hour. Their viability was then assayed by the XTT assay.

Together these results indicate that anisomycin can inhibit cellular senescence in RPE cells subject to oxidative stress.

Example 3: Treatment with H-Leu-Leu-OMe Hydrochloride Stabilizes TAK1 and Increases its Activity in RPE Cells This example demonstrates that LLMe can induce the activity of TAK1 in cultured RPE cells.

RPE cells were obtained and cultured as described. LLMe (Sigma, 1 mM final concentration) was added to RPE cultures and the activity of TAK1 was measured by detection of phosphorylated p38, by western blot, according to standard methods.

Figure 9A:
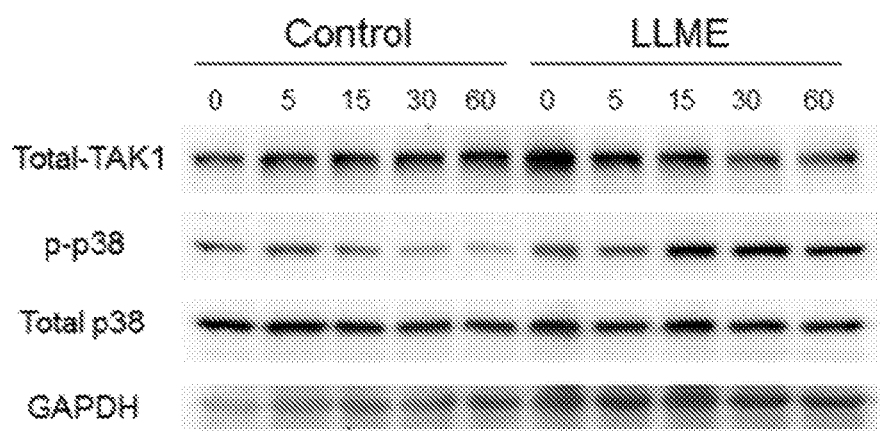
FIGS. 9A-9B: H-Leu-Leu-OMe Hydrochloride stabilizes TAK1 and increases its activity. RPE cells were treated with 1 mM H-Leu-Leu-OMe Hydrochloride or left untreated (control) for the indicated times.
Figure 9B:
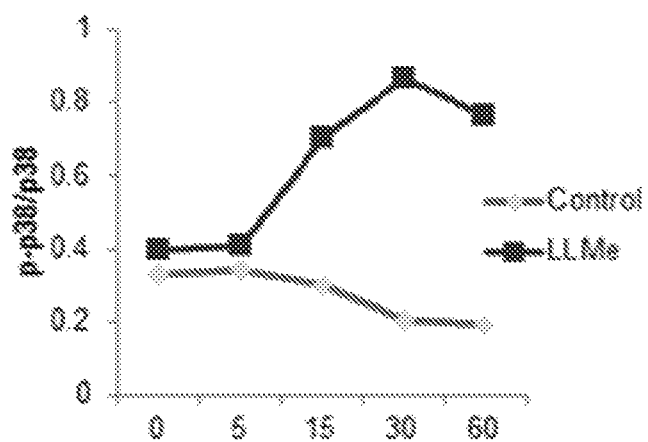

The results of the described experiment to test the effect of LLMe on TAK1 activity/phosphorylation are shown in FIG. 9. As shown in the figure, when RPE cells are treated with LLMe, the activity of TAK1 is increased, as demonstrated by an increase in TAK1-phosphorylated p38. As discussed above, the ability for LLMe to increased TAK1 activity indicates that it will be effective at inhibiting cellular senescence in RPE cells.

Example 4: LLMe Reduces the Senescence Phenotype in A2E Treated RPE Cells

This example shows that LLMe can protect RPE cells from senescence induced by A2E and/or oxidative stress.

All methods are as described. A2E (generated in our laboratory) was added to RPE cultures to a concentration of 5 µM. Oxidative stress was induced by addition of $H_2O_2$ to a concentration of 200 µM. LLMe was added at 1 mM.

Figure 10:
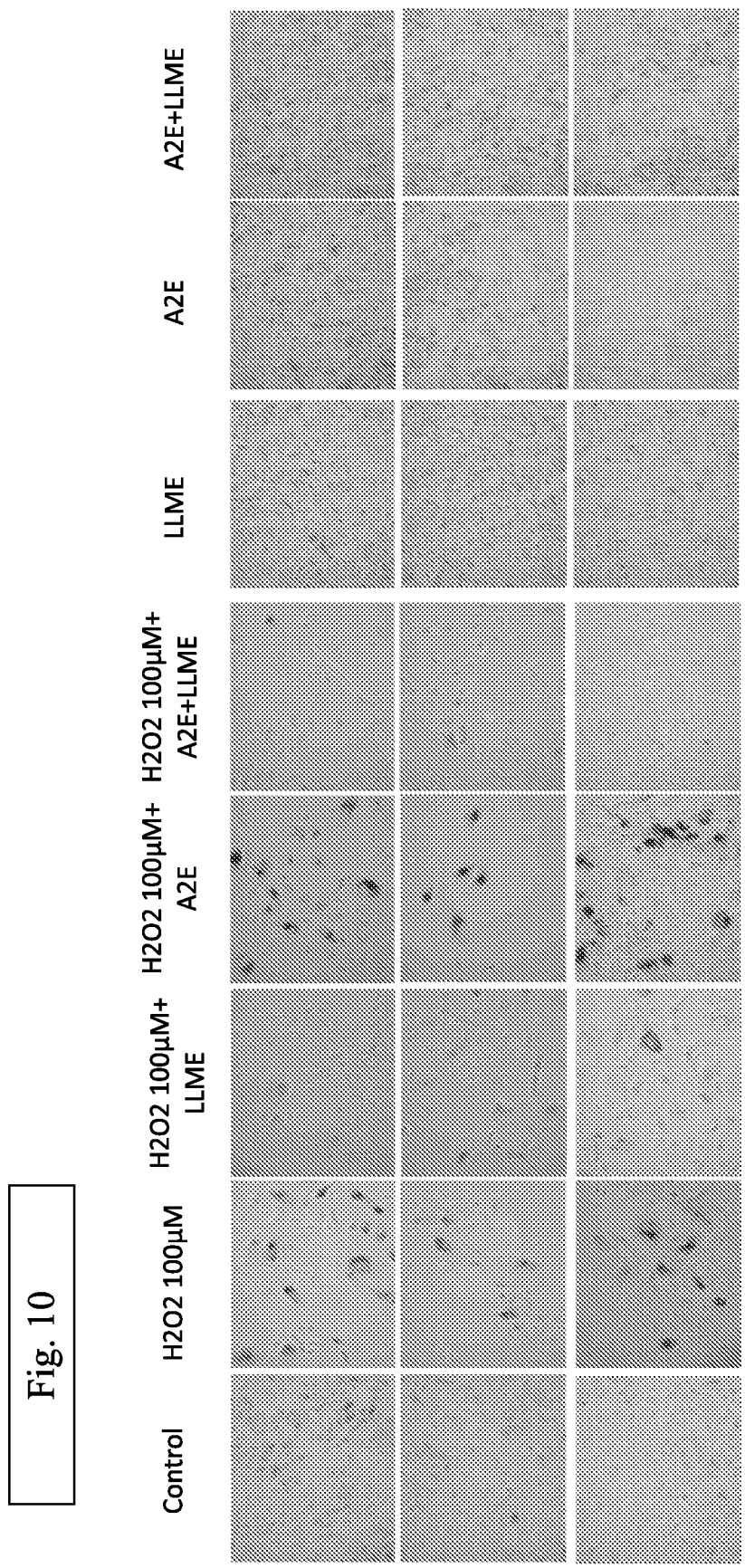
FIG. 10: LLME abolishes the cellular senescence phenotype manifested by SA-β-gal expression in RPE cells subjected to A2E and oxidative stress treatment. Representative photographs showing SA-β-gal staining of RPE cells treated as indicated (treated with $H_2O_2$ (200 µM) for 1 hour and A2E (5 µM) for six hours, with or without LLMe (1 mM). Scale bar, 100 mm.

A2E (pyridinium bisretinoid, a fluorophore of RPE lipofuscin) is one of the elements responsible for the generation the drusen, a hallmark of AMD. Adding A2E to cultured RPE cells increases the senescent phenotype, Furthermore, RPE cells treated with A2E and agents to induce oxidative damage demonstrated an enhanced senescence phenotype manifested by positive SA-β-Gal expression (FIG. 10). In contrast, treatment with LLMe abolished the senescence phenotype in cells treated with A2E alone or in combination with oxidative stress-inducting $H_2O_2$ (FIG. 10).

These results demonstrate that LLMe can abolish the senescence phenotype in RPE cells, and particularly those cells under oxidative stress or with A2E, as a model for drusen accumulation/appearance. Senescent RPE cells are known to be a key factor in the development of AMD. This observation therefore demonstrates that LLMe can be used for treatment of dry AMD and other similar ocular pathologies.

Example 5: Treatment of AMD with LLMe

This example describes the treatment of early stage dry AMD with a pharmaceutical composition that includes H-Leu-Leu-OMe Hydrochloride (LLMe).

Subjects are identified that have been diagnosed with dry AMD. Diagnostic criteria include one or more of detection of retinal drusen; mild vision loss; loss of visual field; abnormal retinal thickness, as determined by OCT imaging; and decreased photoreceptor activity as determined by abnormal ERG results.

Subjects are provided LLMe formulated as eye drops, and instructed to apply one drop in each eye, once a day. In an additional trial, subjects are administered LLMe by intraocular injection once a week. Every two months for the first six months of treatment, subjects are examined for disease progression. Afterwards, subjects are examined every six months. If no change in disease state is detected, subjects are instructed to maintain treatment. If increased drusen or other signs of disease progression are detected, subjects are instructed to increase the LLMe dosage to two or three drops in each eye every day, or are administered additional injections or injections of greater LLMe dosage.

REFERENCES

1. Ambati et al., Neuron 2012, 75:26-39
2. AREDS report no. 8, Archives of ophthalmology 2001, 119:1417-1436
3. Iriyama et al., J Biol Chem 2008, 283:11947-11953
4. Rodier et al., J Cell Biol 2011, 192:547-556
5. Saretzki et al., J Gerontol A Biol Sci Med Sci 1998, 53:B438-442
6. Kozlowski, Medical hypotheses 2012, 78:505-510
7. Nishida et al., Trends in biochemical sciences 1993, 18:128-131
8. Gotoh et al., Enzyme 1993, 38:1625-1628
9. Huangfu et al., J Biol Chem 2006, 281:28802-28810
10. Dimri et al., Proc Natl Acad Sci USA 1995, 92:9363-9367
11. Chuderland et al., Cell Mol Biol Lett 2012, 17:433-445
12. Kim et al. Am J Physiol Renal Physiol 2007, 292:F1471-1478
13. Sakurai et al. Trends in pharmacological sciences 2012, 33:522-530
14. Rufini et al., Oncogene 2013, 32:5129-5143
15. Tyner et al., Nature 2002, 415:45-53
16. Salminen et al., Eur J Neurosci 2011, 34:3-11
17. Coppe J P et al., PLoS One 2010, 5:e9188

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inducing transforming growth factor-beta activated kinase 1 (TAK1) activity in a subject comprising:
    administering to the subject a pharmaceutical composition comprising a therapeutically effective amount of H-Leu-Leu-OMe (LLMe) hydrochloride, LLMe hydrobromide, or a functional derivative thereof,
    wherein diseases treatable by such induction in activity are senescence-related degenerative diseases including Alzheimer's Disease or a retinal degenerative disease selected from the group consisting of dry age-related macular degeneration (AMD), wet AMD, and retinitis pigmentosa.
2. The method of claim 1, further comprising administering to the subject an additional agent for treatment of a senescence-related degenerative disease.

3. The method of claim 2, wherein the additional agent is selected from the group consisting of a TAK1, a TAK1 binding protein (TBP1), and a small molecule.

4. The method of claim 3, wherein the small molecule is anisomycin or a functional derivative thereof.

5. The method of claim 1, wherein the pharmaceutical composition is formulated for injection into the ocular space of the subject, as an ocular ointment, or as eye drops.

6. The method of claim 1, wherein the pharmaceutical composition is incorporated into an ocular implant.

7. The method of claim 1, wherein the LLMe hydrochloride or LLMe hydrobromide inhibits cellular senescence in retinal pigment epithelium (RPE) cells.

\* \* \* \* \*